Aug. 2, 1955 A. E. LANG Plant Pat. 1,408
STRAWBERRY PLANT
Filed Nov. 1, 1954 2 Sheets-Sheet 1
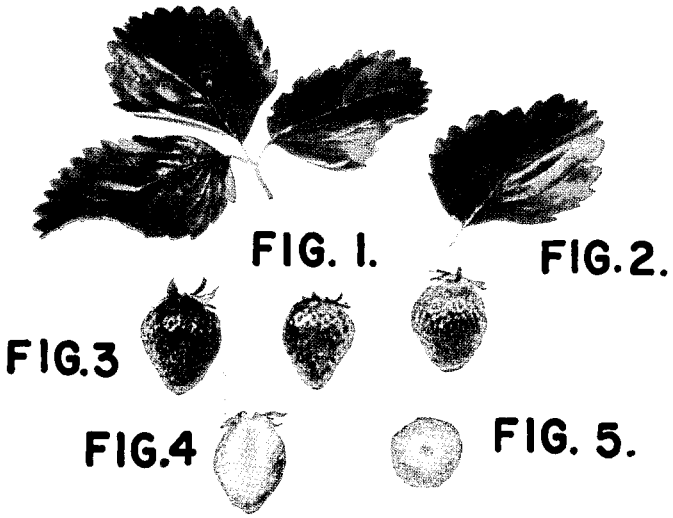
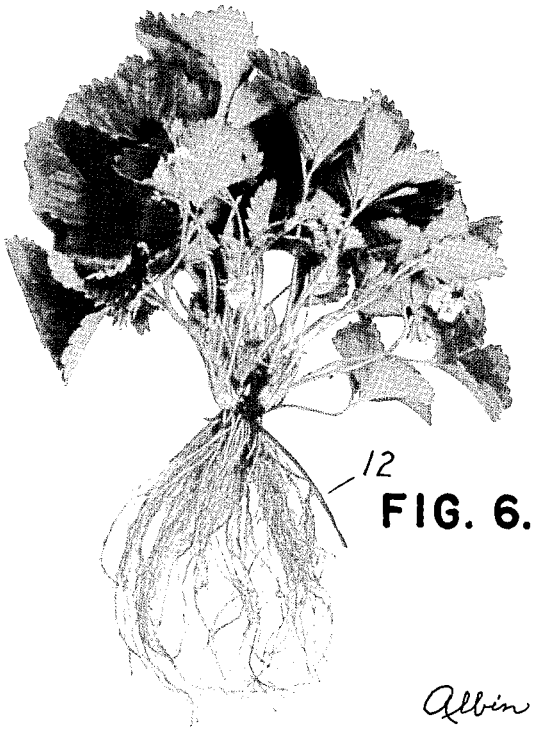
FIG. 6.
Inventor
Albin E. Lang
By William E. Lucas
Attorney Aug. 2, 1955

A. E. LANG

STRAWBERRY PLANT

Plant Pat. 1,408

Filed Nov. 1, 1954

2 Sheets-Sheet 2

Inventor
Albin E. Lang

By William E. Lucas

Attorney

United States Patent Office

Plant Pat. 1,408

Patented Aug. 2, 1955

1,408

STRAWBERRY PLANT

Albin E. Lang, Platteville, Wis.

Application November 1, 1954, Serial No. 466,245

1 Claim. (Cl. 47—62)

My invention relates to a new and distinct variety of strawberry plant. This new and distinct variety is the result of deliberate cross-pollination, under carefully safeguarded conditions, of the Gem everbearing strawberry as the male parent, and the Ambrosia, a June-bearing plant, which I also developed. Neither of the parent plants is patented.

The result of this cross has been the development, through asexual reproduction from the mother plant, which resulted directly from the initial crossing, of a new variety of strawberry, unique and distinct from other varieties in a number of ways, hereinafter related.

The cross-pollination occurred on June 8, 1947. Seed from the fruit so produced was planted in May of 1948, resulting in the mother plant, which was transplanted from hotbed to garden in May of 1951. This mother plant produced fruit and a plurality of runners that summer. The vigor of the plant, its promising fruit, and its production of rooting runners caused and enabled me asexually to reproduce the mother plant further to study its characteristics and merits.

Accordingly, in my said garden in the city of Platteville, Grant County, Wisconsin, beginning in 1951, by transplanting rooted runners and by crown division, I asexually reproduced a large number of plants of my new variety. And I have been able thusly to study the characteristics of the new plant; determine its resistance to extremes of temperature and disease; its production of runners; its multiple crown characteristics; and the quantity and quality of its fruit.

Each successive plant has the same distinctive and unique characteristics exhibited by the mother ancestor. The result of my cross breeding and asexual reproduction has been the development of a distinctly new variety of strawberry plant embodying desirable qualities not heretofore known.

In the accompanying drawings are illustrated typical berries, leaf, leaflet, multiple crown, and crown unit, the two latter with foliage and root systems attached. In said drawings:

Figure 1 illustrates a typical leaf;

Figure 2 illustrates a typical terminal leaflet;

Figure 3 illustrates three typical berries;

Figure 4 shows a central vertical longitudinal section of a typical berry;

Figure 5 depicts a central horizontal section of a typical fruit;

Figure 6 illustrates a side elevation of typical multiple crown with its attached foliage and root systems;

Figures 7, 8:
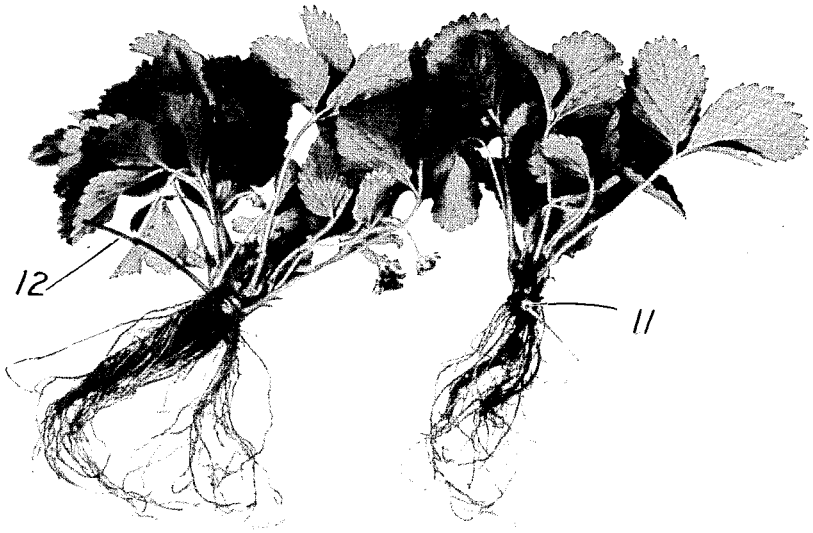
Figure 7 illustrates one of the divided units of the multiple crown of Figure 6.
Figure 8 illustrates the two other units of the multiple crown of Figure 6.

I now specifically refer to the distinguishing characteristics of my new variety of strawberry plant, which characteristics have persisted through successive generations of asexual reproduction and which combine to distinguish my new variety from other known varieties. Among the most unique characteristics are its continuous, all-summer bearing; and the easily-divisible multiple crown, each with its own independent root system.

Coupled with the last-mentioned characteristic is the unique feature that when a crown unit from a fruit-bearing plant is separated and transplanted, in the next season its energies are devoted primarily to the production of fruit, which makes my new variety particularly adapted to the home gardener. On the other hand, when rooted runners are transplanted, many hardy runners in turn are produced, each of which in due time produces a multiple-crown, fruit-bearing plant. Thus my new plant is especially valuable to the truck gardener and nursery man, for each of them simultaneously can have beds that primarily are producing fruit and primarily establishing new plants.

The crown, as I have stated, is composed of a plurality of easily separable units, as shown in Figures 6, 7 and 8. The first crown, of a single unit, which develops from a rooting runner, for example, multiplies by sending out underground shoots which eventually bend upward to establish new units to the crown. The eye of such stem from which the crown unit shown in Figure 7 developed is numbered 11 in Figure 7. Each of these new crown units establishes its own root and foliage systems. By parting the foliage of a multiple-crown plant, the several units of the crown may be observed readily; and may be severed easily with a knife or simply by breaking. A runner stem is shown at 12 in Figures 6 and 8.

When a crown is separated, as above described, into its several units, each having its own root system, the severed units may be transplanted severally with no more setback than would occur if the entire multiple crown were transplanted as a single unit. This is because of the vigorous root system established by each crown unit as shown in Figure 7.

Another chief characteristic distinguishing my new variety is its fruit-producing habit. In a latitude of 42°30′ North it begins blooming about May 10 of a normal year; and continues, without interruption, simultaneously to bloom and bear fruit until a killing frost. Commonly the so-called everbearing strawberry has alternate periods of bearing and rest, producing, for example, a June crop and a late summer or fall crop. On the contrary, my new plant blooms and fruits continuously, not intermittently.

Because of the characteristic of the continuous production of fruit from June until frost with no rest intervals, those strawberry fanciers who are familiar with my new variety refer to it as the "all-summer-bearing" strawberry.

A third principal distinct characteristic is the vigor of the runners. In contact with loose soil, a runner produces roots, two or three leaves, and a blossom stalk almost simultaneously.

Below I summarize a detailed description of my new and distinct variety of strawberry plant:

PLANT CHARACTERISTICS

*Size.*—large, bouquet-shaped.

*Crown.*—composed in an adult plant of a plurality of easily-separable units, each with its own vigorous root and foliage systems.

*Leaves.*—Medium dark green above, glossy when mature; silvery gray beneath. Prominently veined underneath. Unlike in structure and appearance to either parent.

*Leaflets.*—Generally only three; rarely, four. Regularly serrated margins. Do not overlap. A typical terminal leaflet measures three inches long and two and three-fourths inches wide.

*Petiole.*—Rigid, but not as heavy as in the Ambrosia.

*Flower stem.*—Highly pubescent, medium heavy, upright until fruit-laden. Only slightly exposed.

*Runners.*—Hardy and freely produced, except from a transplanted crown unit from a fruit-bearing plant.

*Flower.*—Large size, perfect, self-pollinating. Nearly every blossom produces a marketable berry.

*Drought resistance.*—Good, because of sturdy root system.

*Roots.*—Medium to large. Above average in length. Similar to Ambrosia; more vigorous than Gem.

FRUIT CHARACTERISTICS

*Size.*—Invariably all of salable size, ranging from 2½ to 3½ inches in circumference and from 1¼ to 1¾ inches long. Smaller than Ambrosia; larger than Gem.

*Shape.*—Conical, with rounded nose.

*Aspect.*—Glossy.

*Color.*—Uniformly red.

*Core.*—Small and soft, with reddish color.

*Seeds.*—Bright yellow when ripe, flush with berry's surface. Usually one spot on each berry has dull red seeds.

*Calyx.*—Does not lie against top of berry when latter is ripe.

*Flesh.*—Fine texture, firm, medium juicy.

*Flavor.*—Mildly acid, medium sweet.

*Keeping quality.*—Good.

*Uses.*—Good for canning and freezing.

The strawberry plant above described may vary in degree from the typical characteristics above set forth, depending on soil and weather conditions.

What I claim is:

A new and distinct variety of strawberry plant substantially as herein shown and described, characterized by its habit of continuous bearing of blossoms and fruit from June until frost in a latitude of 42°30′ North; its multiple, easily-divisible crown, each unit of which has its own independent root and foliage systems; its primary production of fruit rather than runners from transplanted crown units; and its essentially simultaneous production of roots, leaves, and flower stems from rooting runners.

No references cited.